United States Patent
O'Dell et al.

(12)

(10) Patent No.: US 6,326,146 B1
(45) Date of Patent: Dec. 4, 2001

(54) METHOD OF DETERMINING MULTIPLE MRNAS IN DYING CELLS

(76) Inventors: Dianne M. O'Dell, 52 Revere Rd., Apt. 10, Drexel Hill, PA (US) 19026; Ramesh Raghupathi, 484 Cassatt Rd., Devon, PA (US) 19312; Tracy Kahl McIntosh, 909 Winding La., Wallingford, PA (US) 19063; Peter Crino, 34 Hemlock Dr., Blenheim, NJ (US) 08012; James Eberwine, 3918 Henry Ave., Philadelphia, PA (US) 19120

( * ) Notice: Subject to any disclaimer, the term of this patent is extended or adjusted under 35 U.S.C. 154(b) by 0 days.

(21) Appl. No.: 09/274,900

(22) Filed: Mar. 23, 1999

Related U.S. Application Data

(60) Provisional application No. 60/079,640, filed on Mar. 27, 1998.

(51) Int. Cl.[7] .............................. C12Q 1/68; C12P 19/34
(52) U.S. Cl. ................................................ 435/6; 435/91.2
(58) Field of Search ........................................ 435/6, 91.2

(56) References Cited

PUBLICATIONS

Eberwine et al. PNAS USA 89:3010–3014, 1992.*
Rink et al. American J. of Path. 147:1575–1583, 1995.*
Rolak. Neurologic Clinics 14:27–43, 1996.*
Salehi et al. Experirntia, 1996, 52:889–891.*

* cited by examiner

*Primary Examiner*—Jeffrey Fredman
*Assistant Examiner*—Juliet C. Einsmann
(74) *Attorney, Agent, or Firm*—Licata & Tyrrell P.C.

(57) ABSTRACT

A method for determining expression levels of multiple mRNAs in single, dying cells from a selected tissue is provided. The method utilizes terminal deoxynucleotidyl-transferase mediated biotin-dUTP nick end labeling to identify dying cells and measures multiple mRNA expression levels in single, isolated dying cells or portions thereof by amplified antisense RNA techniques.

2 Claims, No Drawings

METHOD OF DETERMINING MULTIPLE MRNAS IN DYING CELLS

This application claims the benefit of priority from U.S. provisional application 60/079,640, filed Mar. 27, 1998.

INTRODUCTION

This invention was made in the course of research sponsored by the National Institutes of Health. The U.S. Government may have certain rights in this invention.

BACKGROUND OF THE INVENTION

The ability to assess the expression of multiple genes in individual cells represents a powerful tool for studying the messenger RNA (mRNA) abundances within identifiable cell types. One such technique, the amplified antisense RNA (aRNA) method (Eberwine, J. et al. 1992 *Proc. Natl. Acad. Sci. USA* 89:3010–3014) allows the simultaneous identification of relative messenger RNA (mRNA) levels for multiple genes within single cells. The first introduction of in situ transcription (IST) allowed the analysis of gene expression within fixed tissue sections (Tecott, L. H. et al. 1988 *Science* 240:1661–1664). The recent development of the aRNA procedure coupled with IST permitted the analysis of the relative levels of multiple mRNAs within single, dissociated cells (Eberwine, J. et al. 1992 *Proc. Natl. Acad. Sci. USA* 89:3010–3014). In addition, the aRNA technique can be combined with electrophysiological recordings from dissociated cells (Eberwine, J. et al. 1992 *Proc. Natl. Acad. Sci. USA* 89:3010–3014) or cells from slice preparations (Mackler, S. A. et al. 1992 *Neuron* 9:539–548) to provide a functional correlate of gene expression changes. The cellular specificity of aRNA amplification offers a distinct advantage over other techniques used to evaluate gene expression. For example, Northern analysis involves extraction of RNA from tissue homogenates which include a heterogeneous population of cells particularly within the central nervous system (CNS). In situ hybridization can be used to study gene expression in individual cells, but the study of multiple genes is complex. Another method, PCR, limits analysis to only a few genes at one time (Eberwine, J. et al. 1995 *The Neuroscientist* 1:200–211).

Recently, the aRNA procedure has been extended to characterize the expression of mRNA abundances for multiple genes within immunohistochemically labeled cells (Crino, P. B. et al. 1996 *Proc. Natl. Acad. Sci. USA* 93:14152–14157). This method allows additional phenotypic characterization of cells prior to single cell amplification. While this method of cell identification is useful for identifying cells based on the expression of a particular protein, imamunohistochemical detection is problematic when applied to analyzing the molecular changes in degenerating or dying cells. Specifically, a frequent hallmark of damaged cells is disruption of protein turnover. Therefore, particular proteins may be decreased or even absent in dying cells. Such alterations in protein expression and activity have been reported for a variety of CNS insults (Ferrer, I. et al. 1993 *Clin. Neuropath.* 12:53–58; Taft, W. C. et al. 1993 *J. Cereb. Blood Flow Metab.* 13:796–802; Hicks, R. R. et al. 1996 *Acta Neuropathol.* 91:236–246). However, other proteins are upregulated in neurologic disease (Anderson, A. J. et al. 1994 *Exp. Neurol.* 125:286–295). Thus, the expression of immunohistochemical markers may reveal abnormal cell populations; or alternatively, the expression of certain proteins in cells may be associated with cell death. Without a specific marker of cell damage, however, positive identification of damaged/dying cells based on immunohistochemical criteria is unreliable.

Methods for identifying dying cells by DNA damage stains have been described. For example, terminal deoxynucleotidyl-transferase (Tdt) mediated biotin-dUTP nick end labeling (TUNEL) technique has been used to identify dying cells in a developing brain (Gavrieli et al. 1992 *J. Cell Biol.* 119:493–501). The TUNEL stain utilizes the enzyme Tdt which incorporates biotinylated nucleotides to the 3' ends of fragmented DNA and has been used as a marker for dying cells. This method is useful for identifying cells that are undergoing programmed cell death (PCD), a phenomenon which occurs as a consequence of normal development (Oppenheim, R. W. 1991 *Annual Review of Neuroscience* 14:453–501). TUNEL-positive cells have also been found in pathological conditions including traumatic brain injury (Rink, A. et al. 1995 *Am. J. Pathol.* 147:1575–1583; Colicos, M. A. and Dash, P. K. 1996 *Brain Research* 739:102–131; Conti, A. C. et al. 1996 *J. Neurotrauma* 13:595), ischemia (Li, Y. et al. 1995 *Stroke* 26:1252–1257), tumors (Ikeda, H. et al. 1996 *Am. J. Surg. Pathol.* 20:649–655), Alzheimer's disease (Smale, G. et al. 1995 *Exp. Neurol.* 133:225–230; Tronsco, J. C. et al. 1996 *J. Neuropathol. Exp. Neurol.* 55:1134–1142), Parkinson's disease (Mochizuki, H. et al. 1997 *J. Neural. Transm. Suppl.* 50:125–140), Huntington's disease (Thomas, L. B. et al. 1995 *Exp. Neurol.* 133:265–272), multiple sclerosis (Dowling, P. et al. 1996 *J. Exp. Med.* 184:1513–1518) and amyotrophic lateral sclerosis (ALS); Troost, D. et al., 1995 *Neuropathol. and Applied Neurobiol.* 21:498–504.

SUMMARY OF THE INVENTION

An object of the present invention is to provide a method for determining expression levels of multiple mRNAs in cells undergoing cell death which comprises detecting dying cells in a selected tissue by a DNA damage stain, preferably by a terminal deoxynucleotidyl-transferase mediated biotin-dUTP nick end labeling technique; isolating single, dying cells or portions thereof; and detecting expression levels in these cells or portions thereof by an amplified antisense RNA technique so that expression levels of multiple mRNAs in these cells or portions thereof are determined.

Another object of the present invention is to provide a method of diagnosing diseases of the central nervous system which comprises detecting dying cells in central nervous system tissue by a DNA damage stain, preferably by a terminal deoxynucleotidyl-transferase mediated biotin-dUTP nick end labeling technique; isolating single, dying cells or portions thereof from the tissue; detecting mRNA expression patterns in these cells or portions thereof by an amplified antisense RNA technique; and correlating the pattern of mRNA expression in the dying cells or portions thereof to a disease of the central nervous system.

Another object of the present invention is to provide a method of evaluating therapeutic strategies in diseases of the central nervous system comprising detecting dying cells in central nervous system tissue by a terminal deoxynucleotidyl-transferase mediated biotin-dUTP nick end labeling technique; isolating single, dying cells or portions thereof from the tissue; detecting mRNA expression patterns in these cells or portions thereof by an amplified antisense RNA technique; identifying mRNAs of the expression pattern which are altered; administering agents expected to compensate for alterations in the identified mRNAs; and evaluating the effects of the administered agent on the central nervous system disease.

DETAILED DESCRIPTION OF THE INVENTION

Trauma to the central nervous system (CNS) is frequent in industrialized countries, affecting many patients in the prime of life. The wide variety of diseases of the CNS that involve cell injury and cell death makes understanding the mechanisms behind brain injury a critical element of clinical research. Further, brain trauma is becoming a larger problem for physicians due to advances in emergency medicine that have led to increased survival of patients with injury to the brain and/or spinal cord.

Methods available for studying the changes that occur during development of CNS trauma, or CNS disease that involves cell death, are limited. Much of the focus has been on methods to prevent cell death. Thus, only limited information is available on the physiological changes that occur during CNS cell death and the cellular mediators of cell death. In the present invention, a method for examining the alterations in mRNA expression levels, also referred to herein as expression patterns or profiles, that occur during cell death in single cells is presented. The method involves aRNA amplification techniques for use in cells identified as dying cells by a DNA damage stain, preferably by a terminal deoxynucleotidyl-transferase (Tdt) mediated biotin-dUTP nick end labeling (TUNEL) technique or other marker of DNA damage.

In the method of the present invention, cells in a tissue slice are subjected to a DNA damage stain such as TUNEL for identification of those cells that are dying or undergoing programmed cell death (PCD). Next, in situ transcription (IST) is performed and the single, dying cells or portions thereof are removed from the tissue slice. Multiple mRNA expression levels, also referred to herein as an mRNA expression pattern or profile, are then determined in the single, dying cells or portions thereof by first amplifying the cellular mRNA via an antisense RNA technique followed by expression profiling. By "expression profiling" it is meant that an mRNA expression pattern is determined in the dying cells via a method which comprises converting an mRNA population in the selected cells into cDNA; making the cDNA double stranded; linearly amplifying the double stranded cDNA into aRNA; and using the aRNA as a probe to produce an mRNA expression profile.

Experiments with this method were performed in a rat model of the developing nervous system. Brain tissue from Sprague Dawley P8 rat pups at a stage of development wherein PCD is maximal was used. Brains from these rats were fixed in paraformaldehyde; embedded in paraffin; and sliced into tissue sections. The sections were then subjected to TUNEL and isolated dying cells were subjected to aRNA amplification. Particular cDNAs were chosen for analysis based on mRNAs that were expected to be found in developing cells. Results showed that the mRNAs for nestin, NGF, GAD65, and Bcl-2 were detected in single cells of rat brain undergoing PCD. mRNAs for glial fibrillary acidic protein (GFAP), high molecular weight neurofilament (NF-H), nerve growth factor receptor (NGFR), and tyrosine kinase receptor A (trkA) were not detected by this method, thus indicating an absence of these mRNAs in cells undergoing PCD. The size of the aRNA from TUNEL-positive cells was similar to aRNA generated from surrounding unlabeled cortical cells confirming that aRNA amplification was equally efficient in TUNEL-positive and unlabeled cells.

Experiments were also performed in cells from a traumatic brain injury model. Results from these experiments showed that at 12 hours post-injury, there is an apparent decrease in the mRNA abundances for the genes for nerve growth factor (NGF), cyclic AMP response element binding protein (Creb), tyrosine kinase receptor B (trkB), brain derived neurotrophic factor (BDNF), interleukin-6 (IL-6), Bcl-2, Bcl-$x_L$, glutamate receptors 1 and 2, superoxide dismutase (SOD), nedd-2, β2 microglobulin, red1 and redox factor (Ref-1) in injured, cortical, TUNEL-positive cells exhibiting a non-apoptotic morphology relative to unlabeled, sham-control cortical cells. Additionally, the mRNA abundances did not appear to change as a result of this type of injury for β1 and β2 subunits of the GABA receptor, glutamate receptors 3 and 4, basic fibroblast growth factor (bFGF), trkA, cyclooxygenase (Cox-2), c-Jun, glutamic acid decarboxylase (GAD65), GADPH, NT-3, NT-4, trkC, nerve growth factor receptor (NGF-R, p75), bax, and caspase-3 (CPP-32).

The ability to analyze multiple mRNA levels in TUNEL-stained cells is particularly useful in studying the molecular mechanisms that contribute to cell death. By employing a DNA damage stain such as TUNEL, the method of the present invention avoids problems associated with immunohistochemical labeling of damaged cells because of the decreased synthesis and/or turnover of proteins that accompanies cell damage. By specifically labeling fragmented DNA, TUNEL confirms the presence of dying and/or dead cells. Unlike staining techniques such as Nissl, hematoxylin, acid fuchsin, and silver, TUNEL identifies a specific marker of cell death. Further, the method of the present invention, by combining aRNA with TUNEL, allows for simultaneous analysis of mRNA abundance for numerous genes in a single cell or portion thereof undergoing cell death. The analysis of numerous genes rather than a single gene permits study of the coordinated activation of multiple genes believed to lead to initiation of PCD or necrotic cell death. Further, with the present method, a temporal analysis of coordinated gene expression can be performed in single cells in vivo.

The method of the present invention is also useful in diagnosing CNS diseases in patients suspected of suffering from a CNS disease. TUNEL has been described in a variety of CNS diseases and insults characterized by DNA strand breaks or other DNA damage, including, but not limited to, stroke, cancer, Alzheimer's disease, multiple sclerosis, Parkinson's disease, amyotrophic lateral sclerosis, tumors and Huntington's disease. Accordingly, expression levels of multiple mRNAs in dying cells can be obtained from known diseased CNS tissue samples. Expression patterns from known diseased CNS tissue samples can then be compared to mRNA expression patterns in CNS tissue samples obtained from patients suspected of suffering from a CNS disease. Such samples can be obtained through various surgical procedures including, but not limited to, brain biopsy or temporal lobectomy. Similar mRNA expression patterns are indicative of the patient suffering from the same CNS disease.

The method of the present invention also provides a useful tool for study of the molecular events contributing to cell death in each of these disorders. Further, understanding of the molecular events which occur in these diseases will be useful in development of novel therapeutic approaches for neurological conditions.

In addition, the method of the present invention provides a means for evaluating and/or identifying therapeutic strategies for the treatment of diseases of the central nervous system. In this method, a sample of central nervous system tissue from a patient diagnosed with a central nervous system disease is obtained. Dying cells in the sample of central nervous system tissue are identified by a DNA damage stain such as terminal deoxynucleotidyl-transferase mediated biotin-dUTP nick end labeling technique. Single, dying cells or portions thereof are then isolated from the tissue sample and mRNA expression patterns in these cells or portions thereof are detected by an amplified antisense RNA technique. mRNAs of the expression pattern which are altered, i.e. relative levels are decreased or increased as compared to levels of other mRNAs within the dying cell or in normal cells are then identified and agents expected to compensate for alterations in the identified mRNAs are administered. By "compensate" it is meant that the agent counteracts the biological effects of the altered mRNA levels. Examples of agents which may compensate for the altered mRNA levels include, but are not limited to, vectors expressing a selected gene, proteins encoded by the identified mRNAs, chemical compounds which mimic the activity of these proteins, antisense oligonucleotides which inhibit expression of the identified mRNAs or chemical compounds which inhibit activity of proteins encoded by the identified mRNAs. The effects of the administered agent on the central nervous system disease in the patient are then evaluated.

The following nonlimiting examples are presented to further illustrate the present invention.

EXAMPLES

Example 1

Animal Model for PCD

Sprague Dawley P8 rat pups were anesthetized and decapitated. Skulls were fixed in situ in 4% paraformaldehyde for 3 to 4 hours prior to removal of the brain from the skull. After dissection of the brain, it was immersed and fixed for an additional 24 hours in 4% paraformaldehyde. After fixation, brains were embedded in paraffin and cut into 6 $\mu$m sections.

Example 2

Traumatic Brain Injury Model

Adult male Sprague-Dawley rats weighing 350–400 grams were used. Animals in the injured group were anesthetized with sodium pentobarbital (60 mg/kg, i.p.). Approximately 90 minutes following the pentobarbital injection, rats were placed in a stereotactic frame, the scalp and temporalis muscle were reflected, and a 5.0 mm craniotomy was made over the left parietal cortex midway between bregma and lambda. Rats were subjected to fluid percussion injury of moderate severity (2.4–2.6 atm). Briefly, a female Leur-Lok fitting was attached to the craniotomy site with cyanoacrylate adhesive. After the acrylic hardens, the animal was connected to the injury device which injects a rapid (21–23 millisecond) bolus of saline into the closed cranial cavity producing mechanical deformation of brain tissue. Additional sham control rats were surgically prepared and connected to the injury device but did not receive a fluid pulse.

Example 3

TUNEL

Coronal sections (6 $\mu$M) were adhered to poly-L-lysine coated slides by brief heat treatment at 60° C. for 15 minutes. After deparaffinization and rehydration, the tissue was digested for 15 minutes with proteinase K (20 mg/ml). The reaction was terminated with tap water and the tissue was preincubated in Buffer A (25 mmol/L Tris, pH 6.6) containing 200 mmol/L potassium cacodylate and 0.25 mg/ml bovine serum albumin or BSA) for at least 5 minutes. Sections were incubated at 37° C. with labeling solution containing Tdt (0.3 U/ml), biotinylated-16-dUTP (20 mmol/L), and 1.5 mmol/L cobalt chloride in Buffer A for 1 hour in a humidified chamber. The reaction was terminated with 2×SSC (300 mM sodium chloride and 30 mM sodium citrate, pH 7.4). After vigorous washing with 0.1 M Tris (pH 7.4), the sections were blocked with 10% goat serum in 0.1 A Tris for 30 minutes. The labeled DNA was visualized by treating the tissue with a 1:40 dilution of streptavidin-conjugated alkaline phosphatase and stained with Fast Red. Sections were stored in diethylpyrocarbonate (DEPC)-treated distilled water until further processing.

Example 4

In situ Transcription

Following TUNEL, sections were placed in a humidified chamber and incubated in a mixture of 50% formamide, 5×SSC, DEPC-treated distilled water and an oligo(dt) primer coupled to a T7 RNA polymerase promoter sequence (oligo-dT-T7) that hybridized to cellular poly(A) tail mRNA for 12–18 hours at room temperature. The cDNA was synthesized directly on the section with avian mywloblastosis virus reverse transcriptase (0.5 unit/ml) in IST reaction buffer (50 mM Tris HCl, pH 8.3, 6 mM magnesium chloride, 120 mM potassium chloride, 7 mM dithiothreitol, 250 $\mu$M each dATP, dCTP, dGTP, TTP, and RNAsin at 0.12 unit/ml).

Example 5

Single Cell aRNA Amplification

After TUNEL and IST, individual TUNEL-positive cells (n=2–3 cells per slice) were viewed under 4× magnification and dissected away from the tissue section using an attached micromanipulator and aspirated gently into glass microelectrodes in accordance with procedures described by Crino, P. B. et al. 1996 *Proc. Natl. Acad. Sci. USA* 93:14152–14157. Following second strand synthesis of DNA, the mRNA from cells was amplified with T7 RNA polymerase incorporating [$^{32}$P]CTP as described by Eberwine, J. et al. 1992 *Proc. Natl. Acad. Sci. USA* 89:3010–3014. The aRNA then served as a template for a second round of amplification. The second round radiolabeled aRNA was used to probe reverse Northern (slot) blots.

Example 6

Reverse Northern Blot

To detect particular mRNAs present in single TUNEL-positive cells, reverse Northern blotting was performed using linearized plasmid cDNAs. An array of cDNAs reflecting a sample of the mRNAs found in either developing brain (PCD Model) or injured brain cells (Traumatic Brain Injury model) were selected. In the case of the developing brain these included GAD65, nestin, $\alpha$ internexin, NGF, NGFR, trkA, GFAP, NF-H, and Bcl-2. In the case of the injured brain cells, these included Creb, c-fos, c-jun, GAD 65, $\beta$1, $\beta$2 (subunits of the GABA$_A$ receptor), GluR1–4, NGF, bFGF, BDNF, nt-3, nt-4, trk A, trkB, trkC, NGF-R, IL-6, Bcl-2, Bcl-x$_L$, bax, nedd2, CPP32, Cox-2, SOD, and Ref-1. Nylon membranes (Hybond) were loaded with 0.5 $\mu$g of each cDNA. Blots were then probed with [$^{32}$P]CTP labeled aRNA in hybridization buffer from individual cells and hybridized at 42° C. for 48 hours. Blots were than washed in 2×SSC with 0.1% SDS (2×15 minutes) and then washed in 0.2×SSC with 0.1% SDS for 1 hour. Blots were apposed to film for 48–72 hours.

What is claimed is:

1. A method of diagnosing a patient suspected of suffering from a traumatic brain injury comprising:
   (a) obtaining a sample of brain tissue from a patient suspected of suffering from a traumatic brain injury;

(b) detecting dying cells in said sample of brain tissue by a DNA damage stain;

(c) determining expression levels of multiple mRNAs in the dying cells of the tissue sample obtained from the patient;

(d) comparing the expression levels of multiple mRNAs in the tissue sample obtained from the patient with expression levels of multiple mRNAs determined in known brain injured tissues to diagnose the patient.

2. A method for evaluating therapeutic strategies for treatment of traumatic brain injury in a patient comprising:

(a) obtaining a sample of brain tissue from a patient diagnosed with a traumatic brain injury;

(b) detecting dying cells in said sample by a DNA damage stain;

(c) determining expression levels of multiple mRNAs in the dying cells of the tissue sample obtained from the patient;

(d) identifying mRNAs of the expression pattern which are altered in the dying cells;

(e) administering agents expected to compensate for alteration in the identified mRNAs; and (f) evaluating effects of the administered agent on the brain injured tissue.

* * * * *

UNITED STATES PATENT AND TRADEMARK OFFICE
CERTIFICATE OF CORRECTION

PATENT NO.    : 6,326,146 B1
DATED         : December 4, 2001
INVENTOR(S)   : O'Dell et al.

It is certified that error appears in the above-identified patent and that said Letters Patent is hereby corrected as shown below:

Column 1,
Line 2, please delete "MRNAS" and insert --mRNAS --.
Line 52, please delete "imamunohistochemical" and insert -- immunohistochemical --.

Column 6,
Line 7, please delete "A Tris for 30 minutes" and insert -- M Tris for 30 minutes --.
Line 17, please delete "oligo(dt)" and insert -- oligo(dT) --.
Line 21, please delete "mywloblastosis" and insert -- myeloblastosis --.
Line 29, please delete " under 4X magnification" and insert -- under 40X magnification --.

Signed and Sealed this

Eleventh Day of March, 2003

JAMES E. ROGAN
*Director of the United States Patent and Trademark Office*